United States Patent
Yachi

(10) Patent No.: US 10,736,597 B2
(45) Date of Patent: Aug. 11, 2020

(54) RADIOGRAPHIC APPARATUS, RADIOGRAPHIC SYSTEM, CONTROL METHODS THEREOF, AND COMPUTER-READABLE STORAGE MEDIUM

(71) Applicant: CANON KABUSHIKI KAISHA, Tokyo (JP)

(72) Inventor: Katsuya Yachi, Zama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 14 days.

(21) Appl. No.: 16/261,995

(22) Filed: Jan. 30, 2019

(65) Prior Publication Data

US 2019/0250109 A1 Aug. 15, 2019

(30) Foreign Application Priority Data

Feb. 14, 2018 (JP) ................................. 2018-024336

(51) Int. Cl.
*A61B 6/00* (2006.01)
*H05G 1/56* (2006.01)
*H05G 1/26* (2006.01)

(52) U.S. Cl.
CPC ................ *A61B 6/54* (2013.01); *A61B 6/582* (2013.01); *H05G 1/26* (2013.01); *H05G 1/56* (2013.01)

(58) Field of Classification Search
CPC ........... A61B 6/54; A61B 6/542; A61B 6/545; A61B 6/582; A61B 6/548; H05G 1/26; H05G 1/56
See application file for complete search history.

(56) References Cited

U.S. PATENT DOCUMENTS

| 7,894,575 B2 | 2/2011 | Tsubota et al. |
| 9,961,761 B2 | 5/2018 | Yachi |
| 10,139,499 B2 | 11/2018 | Yachi |
| 2017/0156689 A1* | 6/2017 | Shinotsuka ............ A61B 6/461 |
| 2020/0037426 A1* | 1/2020 | Uchiyama ................ H05G 1/42 |

FOREIGN PATENT DOCUMENTS

JP 2010-081960 4/2010

* cited by examiner

*Primary Examiner* — Chih-Cheng Kao
(74) *Attorney, Agent, or Firm* — Venable LLP

(57) ABSTRACT

A radiographic system comprises: an irradiation control apparatus including a first timer configured to provide a time value for an irradiation timing; and a radiographic apparatus that is communicably connected to the irradiation control apparatus and includes a second timer configured to provide a time value for an imaging timing. The system measures a time difference between a time value of the first timer and a time value of the second timer; corrects at least one timer out of the first timer and the second timer so as to eliminate the time difference using one of a plurality of types of correction processing having different correction periods. The correction processing to be used is selected from the plurality of types of correction processing, based on an operating state of the radiographic apparatus.

14 Claims, 12 Drawing Sheets

RADIOGRAPHIC APPARATUS, RADIOGRAPHIC SYSTEM, CONTROL METHODS THEREOF, AND COMPUTER-READABLE STORAGE MEDIUM

BACKGROUND OF THE INVENTION

Field of the Invention

The present invention relates to a radiographic apparatus, a radiographic system, control methods thereof and computer-readable storage medium.

Description of the Related Art

A radiographic apparatus and a radiographic system in which a radiation image obtained from radiation emitted from a radiation generator and transmitted through a subject is converted into a digital image, and the digital image undergoes image processing to obtain sharp radiation image data are commercially available.

In such a radiographic apparatus, a two-dimensional solid-state image sensor is generally used as a radiation detector. The radiation detector converts the emitted radiation into charges, accumulates the charges in a capacitor, and repeats the readout and reset operation of the accumulated charges. In an image sensor without an electronic shutter, when radiation irradiation is made on the image sensor at the time of charge readout and reset operation, charges nonrelated to the radiation imaging are superimposed on the radiation image, thereby degrading the quality of the radiation image. For this reason, in a radiographic system, the operation timing of a radiation detector in the radiographic apparatus must be synchronized with the irradiation timing of the radiation generator.

Japanese Patent Laid-Open No. 2010-081960 (to be referred to as a patent literature 1 hereinafter) describes a radiographic system in which an electronic cassette and a console for controlling the radiation generator include timer units, respectively, and the radio clock functions are imparted to the two timers, respectively, thereby implementing synchronization between the two timer units. By using such a radio clock function, the reference electromagnetic signal representing a reference time is received to correct the time.

In the arrangement of patent literature 1, the times are synchronized using a reference externally given as the reference electromagnetic signal. For example, even if a time shift (time difference) during imaging of the radiation image occurs, the time difference (shift) cannot be eliminated unless the reference electromagnetic signal is received. If the time shift is corrected upon receiving the reference electromagnetic signal during imaging of the radiation image, the imaging time (charge accumulation time of radiation) is changed by correction if a correction amount is large, thereby degrading the quality of the radiation image. Accordingly, a demand has arisen for accurately performing time synchronization between the timer which obtains the radiation irradiation timing and the timer which obtains a radiation radiographic timing and for reducing an influence of time correction on radiation imaging.

SUMMARY OF THE INVENTION

According to one aspect of the present invention, there is provided a radiographic system in which an irradiation control apparatus configured to control irradiation of radiation and a radiographic apparatus configured to perform radiation imaging are communicably connected, the system comprising: a first timer incorporated in the irradiation control apparatus and configured to provide a time value for an irradiation timing; a second timer incorporated in the radiographic apparatus and configured to provide a time value for an imaging timing; a measurement unit configured to measure a time difference between a time value of the first timer and a time value of the second timer; a correction unit configured to correct at least one timer out of the first timer and the second timer so as to eliminate the time difference, the correction unit capable of executing a plurality of types of correction processing having different correction periods; and a selecting unit configured to select, from the plurality of types of correction processing, correction processing to be executed by the correction unit, based on an operating state of the radiographic apparatus.

According to another aspect of the present invention, there is provided a radiographic apparatus that performs radiation imaging using radiation emitted from an irradiation control apparatus, comprising: a communication unit configured to communicate with the irradiation control apparatus; a timer unit configured to provide a time value for a timing of the radiation imaging; a measurement unit configured to measure a time difference between the time value of the timer unit and a time value of a timer of the irradiation control apparatus by communication via the communication unit; a correction unit configured to correct the timer unit so as to eliminate the time difference, the correction unit capable of executing a plurality of pieces of correction processing having different correction periods; and a selecting unit configured to select, from the plurality of pieces of correction processing, correction processing to be executed by the correction unit, based on an operating state of the radiographic apparatus.

According to another aspect of the present invention, there is provided a control method for a radiographic system in which an irradiation control apparatus incorporating a first timer that provides a time value for an irradiation timing and configured to control irradiation of radiation and a radiographic apparatus incorporating a second timer that provides a time value for imaging timing are communicably connected to each other, the method comprising: measuring a time difference between the time value of the first timer and the time value of the second timer; selecting, from a plurality of types of correction processing having different correction periods, correction processing based on an operating state of the radiographic apparatus, the selected correction processing being configured to correct at least one of the first timer and the second timer so as to eliminate the time difference; and executing the selected correction processing.

According to another aspect of the present invention, there is provided a control method for a radiographic apparatus including a communication unit configured to communicate with an irradiation control apparatus and timer unit configured to provide a time value for a timing of radiation imaging, the radiographic apparatus performing the radiation imaging using radiation emitted from the irradiation control apparatus, the method comprising: measuring a time difference between the time value of the timer unit and a time value of a timer of the irradiation control apparatus by communication via the communication unit; selecting, from a plurality of types of correction processing having different correction periods, correction processing based on an operating state of the radiographic apparatus, the selected correction processing being configured to correct the timer unit so as to eliminate the time difference; and executing the selected correction processing.

Furthermore, according to another aspect of the present invention, there is provided a non-transitory computer-readable storage medium storing a program for causing a computer to execute a control method for a radiographic apparatus including a communication unit configured to communicate with an irradiation control apparatus and timer unit configured to provide a time value for a timing of radiation imaging, the radiographic apparatus performing the radiation imaging using radiation emitted from the irradiation control apparatus, the method comprising: measuring a time difference between the time value of the timer unit and a time value of a timer of the irradiation control apparatus by communication via the communication unit; selecting, from a plurality of types of correction processing having different correction periods, correction processing based on an operating state of the radiographic apparatus, the selected correction processing being configured to correct the timer unit so as to eliminate the time difference; and executing the selected correction processing.

Further features of the present invention will become apparent from the following description of exemplary embodiments (with reference to the attached drawings).

DESCRIPTION OF THE EMBODIMENTS

Embodiments of the present invention will be described in detail with reference to the accompanying drawings. Note that details of sizes and structures shown in the respective embodiments are not limited to the specification and drawings. Note that radiation includes an X-ray, an α-ray, a β-ray, a γ-ray, and various kinds of particle beams.

First Embodiment

Figure 1:
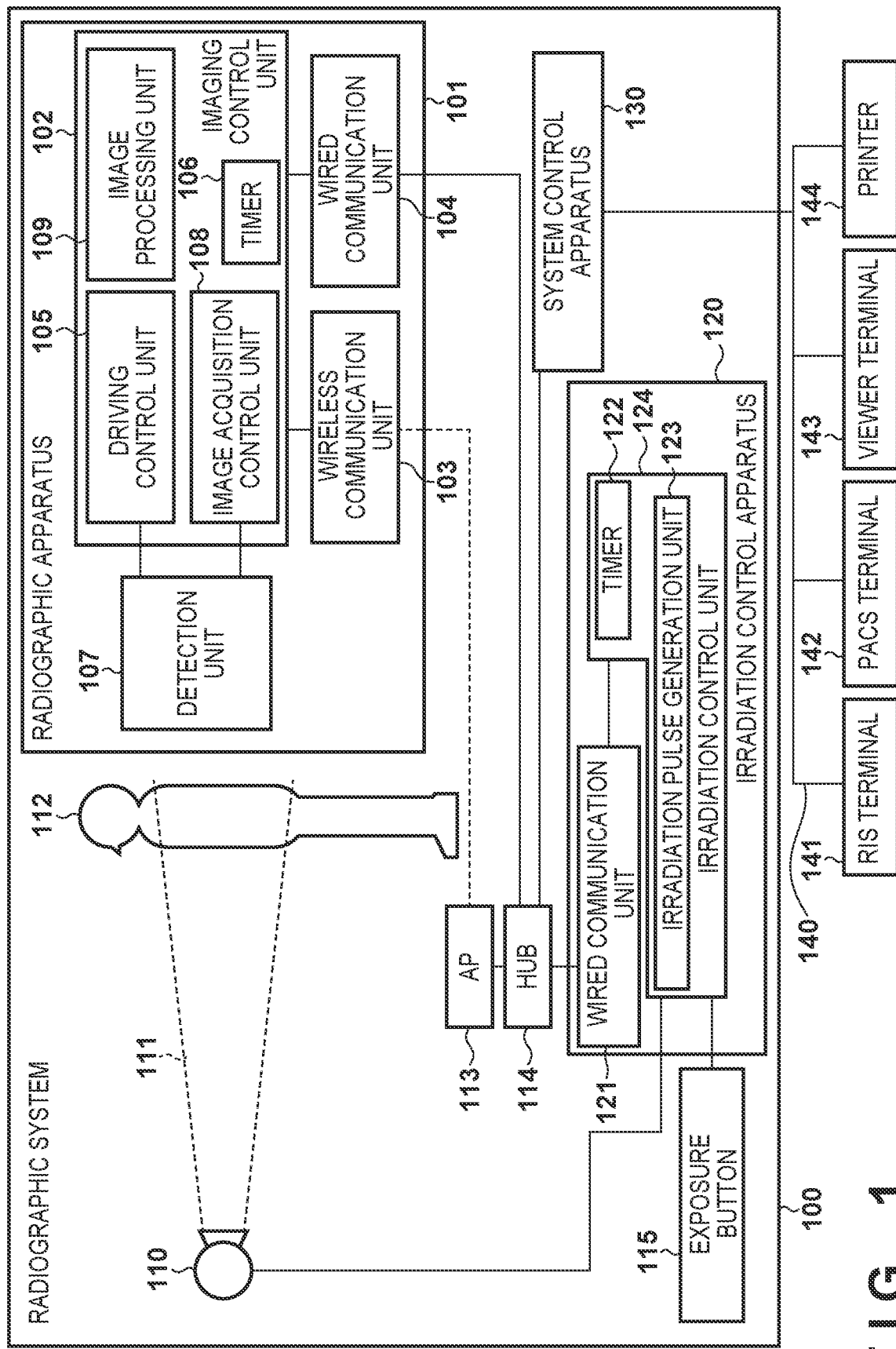
FIG. 1 is a block diagram showing an example of the arrangement of a radiographic system according to the first embodiment.

FIG. 1 is a block diagram showing an example of the arrangement of a radiographic system 100 according to the first embodiment. The radiographic system 100 includes a radiographic apparatus 101, a radiation generator 110, an irradiation control apparatus 120 for controlling the radiation generator 110, and a system control apparatus 130. In the radiographic system 100, the irradiation control apparatus 120 for controlling radiation irradiation and the radiographic apparatus 101 for performing radiation imaging are communicably connected, as will be described later.

In the radiographic system 100, an operator can set conditions necessary for imaging using an operation device (not shown) and a display device (not shown) connected to the system control apparatus 130. The system control apparatus 130 outputs irradiation information for radiation irradiation including the set conditions. The irradiation information output from the system control apparatus 130 is received by the irradiation control apparatus 120 and used for operation settings in the radiation generator 110. The irradiation control apparatus 120 causes the radiation generator 110 to emit radiation upon pressing of an exposure button 115. The radiation emitted by the radiation generator 110 is transmitted through a subject 112 and imaged by the radiographic apparatus 101. A radiation image obtained by the radiographic apparatus 101 is transferred to the system control apparatus 130. The system control apparatus 130 performs, for example, necessary image processing and the like for the transferred radiation image and outputs the processed radiation image to the display device. Note that the system control apparatus 130, the display device (not shown), and the operation device (not shown) may be integrated. Alternatively, an RIS terminal 141 and a viewer terminal 143 to be described later can be used as the above-mentioned display device and operation device connected to the system control apparatus 130.

The irradiation control apparatus 120 includes a wired communication unit 121 and an irradiation control unit 124. The irradiation control unit 124 includes a timer 122 and an irradiation pulse generation unit 123. The irradiation control unit 124 performs various kinds of control in the irradiation control apparatus 120. The irradiation control apparatus 120 is communicably connected to the system control apparatus 130 via the wired communication unit 121. The irradiation control unit 124 outputs, to the radiation generator 110, a signal for radiation irradiation timing control generated by the irradiation pulse generation unit 123 using the timer 122 as a reference. The exposure button 115 is formed from, for example, a hand switch, a foot switch, or the touch screen of a portable terminal. The exposure button 115 is used for control of a static imaging irradiation timing, an irradiation timing of dynamic imaging such as fluoroscopy, and irradiation period control. The timer 122 incorporated in the irradiation control apparatus 120 provides a time value for synchronizing the driving timing of the radiographic apparatus 101 with the irradiation timing of the radiation from the radiation generator 110. The precision required for the timer 122 is decided by an error which is allowed in the synchronization operation with the radiographic apparatus 101. In dynamic imaging which requires higher synchronization precision than that in static imaging, for example, it is desirable to allow the timer 122 to make it possible to adjust the precision of the radiation irradiation pulse width or less.

The radiation generator 110 includes, for example, an X-ray tube, an irradiation mechanism, and a collimation mechanism. The radiation generator 110 emits radiation in a pulsed or continuous form using a tube voltage and tube current corresponding to a driving signal from the irradiation control apparatus 120. In addition, the radiation generator 110 may include a display unit for displaying radiographic conditions, radiographic images, and the like. The radiation emitted by the radiation generator 110 is imaged by the radiographic apparatus 101 synchronized with the irradiation timing.

The radiographic apparatus 101 includes an imaging control unit 102 and a detection unit 107 in which pixels for converting radiation into an electrical signal are arrayed two-dimensionally. The imaging control unit 102 performs various kinds of control in the radiographic apparatus 101. The imaging control unit 102 includes a driving control unit 105, a timer 106, an image acquisition control unit 108, and an image processing unit 109. The driving control unit 105 performs driving control of the detection unit 107. The timer 106 is incorporated in the radiographic apparatus 101 and used to synchronize the driving timing of the radiation irradiation by the irradiation control apparatus 120 with the driving timing of the detection unit 107. That is, the timer 106 provides a time value for the imaging timing of radiation imaging using the detection unit 107 by the imaging control unit 102. The image acquisition control unit 108 performs processes associated with saving of radiation image data obtained from the detection unit 107, determination of the transfer timing of the radiation image data, radiation image data transfer control, and the like. The image processing unit 109 performs various kinds of image processing for the image data acquired from the detection unit 107.

As will be described later, in radiation dynamic imaging, the radiation irradiation by the irradiation control apparatus 120 is synchronously operated with the radiation imaging by the radiographic apparatus 101 using the timers 122 and 106.

In the radiographic system 100, the radiographic apparatus 101, the irradiation control apparatus 120, and the system control apparatus 130 are communicably connected to each other via a wireless or wired communication network. A wireless communication unit 103 and/or the wired communication unit 104 of the radiographic apparatus 101 and the wired communication unit 121 of the irradiation control apparatus 120 are connected to this communication network. The communication network includes a wireless LAN access point (AP) 113 and a network switch (HUB) 114. Information is exchanged in the form of a message between the devices connected via the communication network. It is possible to determine a connection state between the devices and automatically switch the communication to wired communication if the wired connection is made. Note that a system including both the wireless communication and the wired communication is exemplified, but it is possible to construct a system using one of these communication methods.

In addition, in the radiographic system 100, the radiation generator 110 is electrically directly connected to the irradiation control apparatus 120 without being through the communication network. Information is not converted into the form of a message, but is transmitted directly as an electrical signal between the radiation generator 110 and the irradiation control apparatus 120. Since electrical direct connection is highly reliable, it is suitable for the connection between the radiation generator 110 and the irradiation control apparatus 120. As a matter of course, the radiation generator 110 and the irradiation control apparatus 120 can be connected using the communication network.

The radiographic system 100 is connected to the RIS terminal 141, a PACS terminal 142, the viewer terminal 143, and a printer 144 via a communication unit 140 such as a network. RIS stands for Radiology Information System, and PACS stands for Picture Archive and Communication System.

The RIS terminal 141 is an operation terminal connected to the radiographic system 100 and constitutes an information system in the radiology department. This information system is an information management system for comprehensively managing, for example, a radiation image or information added to an examination order. The added information includes examination information indicating an examination ID or receipt number. The operator can input an examination order (examination instruction) via the RIS terminal 141, and the radiographic system 100 can perform imaging in accordance with this examination order. Note that in this embodiment, although the input examination order can be saved and managed by the RIS terminal 141, the input examination order may be saved and managed by a server (not shown) connected to the MS terminal 141 and the radiographic system 100. Alternatively, the input examination order may be saved and managed by the radiographic system 100.

The PACS terminal 142 saves and manages a radiographic image obtained by the radiographic system 100. That is, the PACS terminal 142 functions as part of the image management system for managing the radiographic image. The viewer terminal 143 displays and outputs a radiation image saved in the PACS terminal 142. The printer 144 outputs the radiation image saved in the PACS terminal 142 to a medium such as a film.

The operator obtains a radiation image using the radiographic system 100 based on the examination order including a plurality of examination information input via the RIS terminal 141. The examination information includes imaging protocol information. The imaging protocol information includes parameter information (imaging execution information) used at the time of imaging or image processing and imaging environment information such as a sensor type or an imaging posture. Parameters such as a frame rate, the length of a radiation pulse per frame, and the like are set in the imaging protocol for dynamic imaging. In addition, the examination information includes information for specifying the examination order such as the examination ID and the receipt number, and information for specifying the radiation image based on the examination order.

Figure 2:
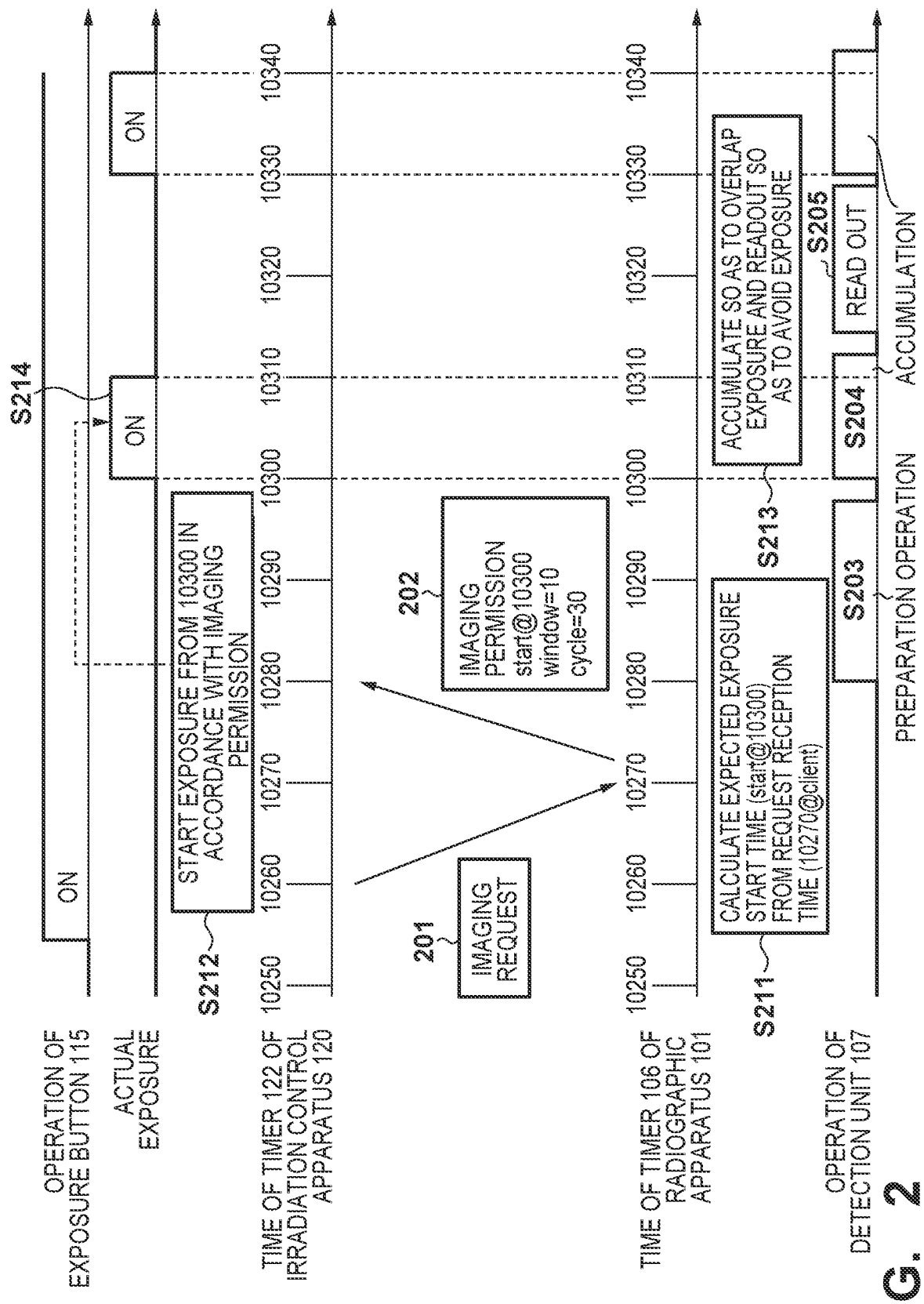
FIG. 2 is a timing chart showing a message communication operation for controlling the start of imaging.

An operation timing for communicating a message for controlling the start of imaging in the radiographic system 100 of this embodiment will be described in detail with reference to FIG. 2. Upon pressing the exposure button 115, the irradiation control apparatus 120 transmits a message of an imaging request 201 to the radiographic apparatus 101. The radiographic apparatus 101 adds a predetermined time to the time (request reception time) at which the message of the imaging request 201 has been received and calculates expected exposure start time (step S211). The predetermined time to be added here is a time with a sufficient margin to perform message exchange and a preparation operation of the radiographic apparatus 101, and at the same time is suitable to be a short time so as not to degrade the operation feeling while the operator unnecessarily waits for the operation. In the example of FIG. 2, "30" is used as the predetermined time, and the expected start time "10300" is calculated from the request reception time "10270". Alternatively, this predetermined time may be set by manual calculation at the time of system design or may be dynamically decided by pre-negotiation using communication between the irradiation control apparatus 120 and the radiographic apparatus 101.

Upon reception of the imaging request 201, the radiographic apparatus 101 transmits a message of imaging permission 202 in which the expected exposure start time (start@) is included as a parameter. Note that the message of the imaging permission 202 includes pieces of information corresponding to the length (window=) of the radiation pulse and a frame rate (cycle=) in FIG. 2. Note that these pieces of information need not be included in this message. As described above, the pieces of information may be set by another means in advance prior to imaging, or a parameter which is not explicitly indicated here may be included in this message, and the resultant message may be transmitted.

The irradiation control apparatus 120 outputs an irradiation pulse from the irradiation pulse generation unit 123 in accordance with the expected exposure start time indicated by the received message of the imaging permission 202 (step S212). That is, the irradiation control apparatus 120 waits for the time indicated by the timer 122 to reach the expected exposure start time and starts generation of the irradiation pulse. If the message includes the length information of the radiation pulse and the frame rate information as described above, the irradiation control apparatus 120 generates an irradiation pulse for performing exposure in accordance with these pieces of information. Note that the length of the radiation pulse and the frame rate may be determined in advance, as described above. Subsequently, the irradiation control unit 124 of the irradiation control apparatus 120 plans an operation based on the time of the timer 122 so as to acquire a radiation image based on the predetermined length of the radiation pulse and the predetermined frame rate, thereby causing the irradiation pulse generation unit 123 to generate the irradiation pulse (step S214).

On the other hand, the radiographic apparatus 101 performs, in accordance with the expected exposure start time, an accumulation operation so as to include an exposure period and reads out the radiation image from the detection unit 107 in a period excluding the exposure (step S213). That is, the radiographic apparatus 101 transmits the message of the imaging permission 202 and then performs the preparation operation (step S203) for imaging. When the time indicated by the timer 106 reaches the expected exposure start time, the operation of the detection unit 107 is set in the accumulation state for the radiation irradiation (step S204). If a time has elapsed by the length of the radiation pulse after the transition to the accumulation state (after the time indicated by the timer 106 reaches 10310 in FIG. 2), the radiation image is read out from the detection unit 107 (step S205). After that, as in the irradiation control apparatus 120, the radiographic apparatus 101 plans the accumulation operation and the readout operation based on the time of the timer 106 so as to acquire an image at a predetermined frame rate, and executes these operations.

As described above, the irradiation control apparatus 120 generates the irradiation pulse under the condition that the message of the imaging permission 202 is received. In a case where a message loss or a large delay occurs in the communication network and the radiographic system 100 cannot receive the assumed message, the irradiation control apparatus 120 does not start radiation irradiation or stops it. For example, the above-described case is a case in which the imaging permission 202 cannot be received within the predetermined time after the irradiation control apparatus 120 transmits the imaging request 201, or a case in which the arrival time of the message of the imaging permission 202 in the irradiation control apparatus 120 has passed the expected exposure start time indicated by the message. Note that if the irradiation control apparatus 120 cannot receive the message of the imaging permission 202 transmitted from the radiographic apparatus 101 or the message reception is delayed, the radiographic apparatus 101 cannot know whether the message loss occurs. In this case, the radiographic apparatus 101 starts acquisition of the radiation image data and as a result acquires an image obtained without irradiation. However, this operation is an operation in which extra radiation irradiation is not performed for the subject, that is, a safe operation for the subject.

Note that an event in which the message of the imaging permission 202 does not reach the irradiation control apparatus 120 until the expected exposure start time does not occur by only the message loss described above. Such an event can be considered as cases (1) to (3) below. In any case, extra radiation irradiation for the subject can be avoided.

(1) A case in which the radiographic apparatus 101 does not transmit the message of the imaging permission 202 because the message of the imaging request 201 is lost.
(2) A case in which the message of the imaging request 201 is delayed.
(3) A case in which the radiographic apparatus 101 determines that the execution of the radiation imaging is impossible due to a reason on the side of the radiographic apparatus 101 and does not respond. In this case, the radiographic apparatus 101 preferably responds, to the irradiation control apparatus 120, an imaging disable message in place of the message of the imaging permission 202.

In the radiographic system 100, during pressing of the exposure button 115, imaging (dynamic imaging) of a radiation image is performed at the set frame rate. If the operator stops pressing the exposure button 115 to end imaging, the irradiation control apparatus 120 stops generating the timing pulse for radiation irradiation, generates a message indicating the stop of imaging, and transmits it to the radiographic apparatus 101.

Figure 3:
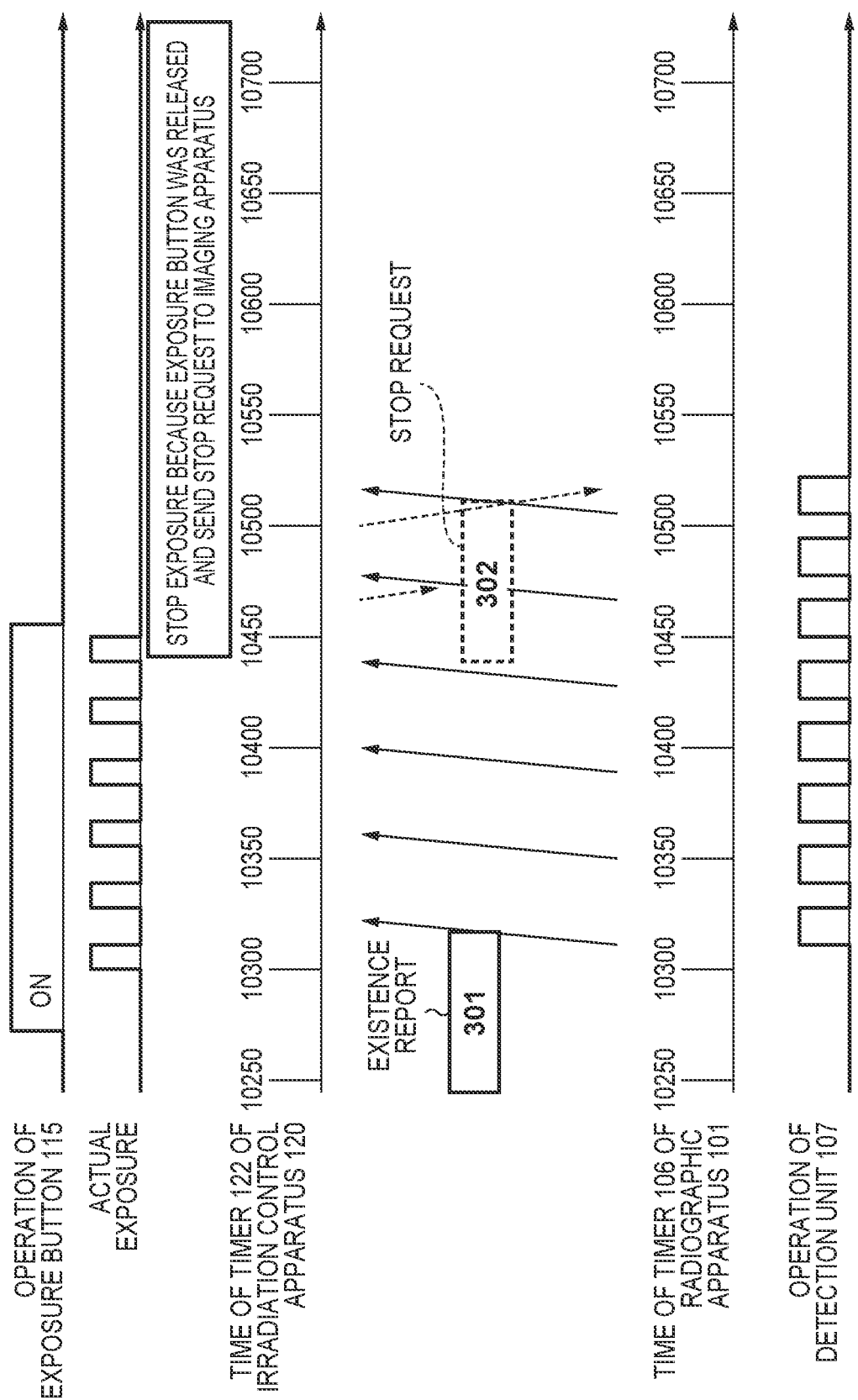
FIG. 3 is a timing chart showing message communication operation during radiation imaging and at the end of radiation imaging.

FIG. 3 shows the exchange of commands between the irradiation control apparatus 120 and the radiographic apparatus 101 during imaging and at the end time of imaging. During imaging, the radiographic apparatus 101 periodically transmits a message of an existence report 301 to the irradiation control apparatus 120. Upon reception of the periodically transmitted message of the existence report 301, the irradiation control apparatus 120 determines that imaging is normally performed. If the message of the existence report 301 is interrupted, the irradiation control apparatus 120 determines that the radiographic apparatus 101 is not set in a status for receiving irradiation, and stops radiation irradiation, thereby interrupting imaging. If the exposure button 115 is set in an OFF state, the irradiation control apparatus 120 stops radiation irradiation and transmits a message of a stop request 302 to the radiographic apparatus 101. Upon reception of the message of the stop request 302, the radiographic apparatus 101 determines that imaging ends.

Figure 4:
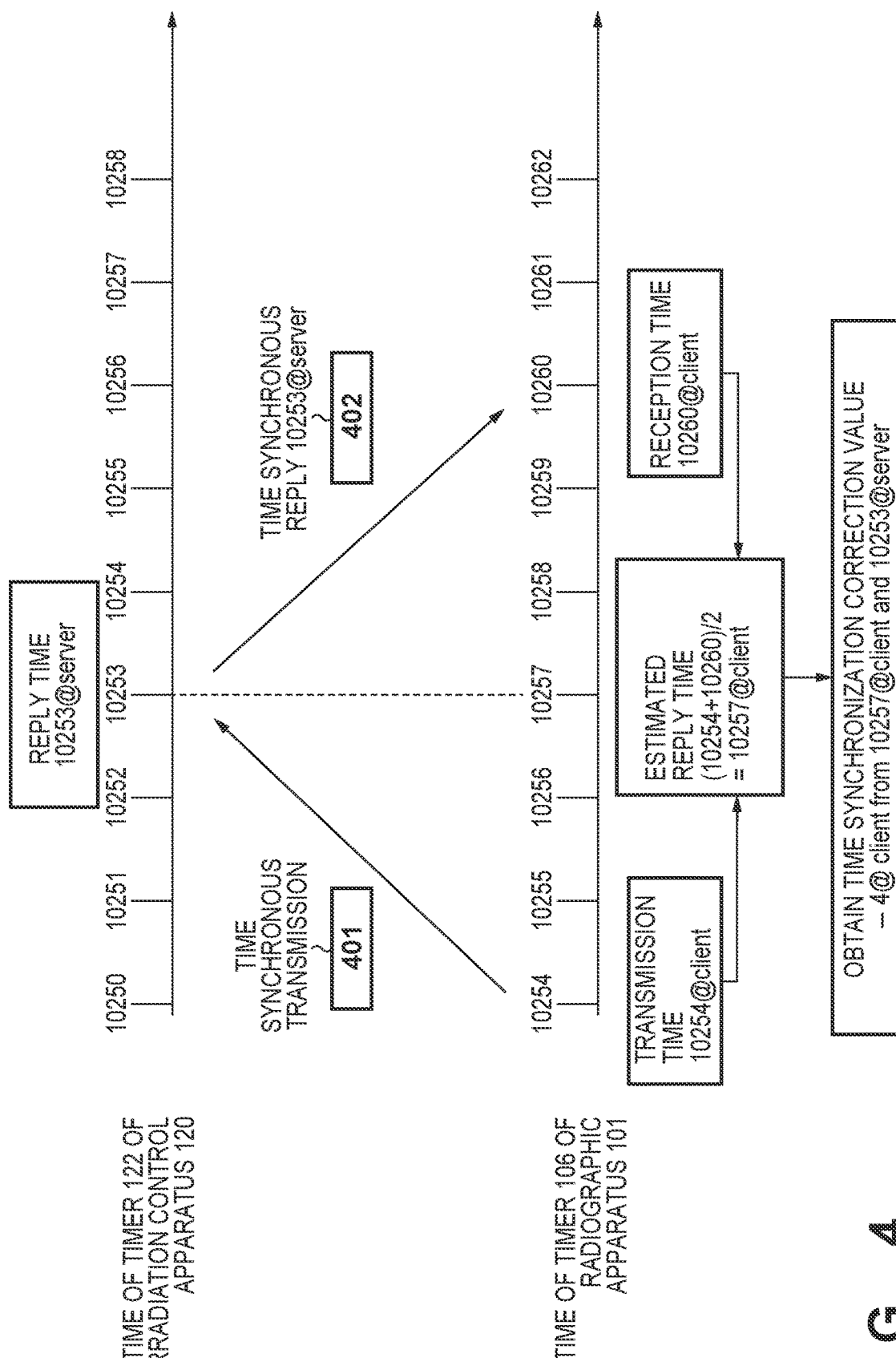
FIG. 4 is a timing chart showing an operation for measuring a difference between pieces of time information of apparatuses.

FIG. 4 is a view showing the sequence for measuring a difference (time difference) between the timer 106 and the timer 122 via the communication on the communication network in order to implement synchronization between time values of the timer 106 and the timer 122. This processing will be performed by a measurement unit 521 (to be described later with reference to FIG. 5) for measuring the time difference between the timer 106 and the timer 122. In FIG. 4, the timer 122 operates as a timer as a time server, that is, a time reference, while the timer 106 operates as a time client, that is, a timer which operates following the time server. First, the radiographic apparatus 101 transmits a message of time synchronous transmission 401 to the irradiation control apparatus 120 via the wired communication unit 104 or the wireless communication unit 103. At this time, the radiographic apparatus 101 records time (transmission time) at the time of transmission indicated by the timer 106. In the example of FIG. 4, a time value "10254" is recorded as the transmission time. The irradiation control apparatus 120 having received the message of the time synchronous transmission 401 immediately replies a message of a time synchronous reply 402. At this time, the irradiation control apparatus 120 includes, in the message of the time synchronous reply 402, as reply time, time given at the time of reply indicated by the timer 122. In the example of FIG. 4, a time value "10253" is included.

Upon reception of the message of the time synchronous reply 402, the radiographic apparatus 101 acquires this time as the reception time from the timer 106. In the example of FIG. 4, a time value "10260" is acquired as the reception time. The radiographic apparatus 101 estimates the time of the timer 106 at which the irradiation control apparatus 120 replies the message of the time synchronous reply 402. The time obtained by this estimation is given as estimated reply time. More specifically, the radiographic apparatus 101 assumes that the transmission times of the messages of the time synchronous transmission 401 and the time synchronous reply 402 are equal to each other, calculates an intermediate value between the transmission time and the reception time, and defines this as the estimated reply time.

In the example of FIG. 4, an intermediate value between the transmission time "10254" and the reception time "10260", that is, (10254+10260)/2=10257 is decided as the estimated reply time. Since the reply time included in the message of the time synchronous reply 402 is given as "10253", the radiographic apparatus 101 calculates a difference between the reply time and the estimated reply time and determines that the time of the timer 106 advances as compared with the timer 122 by 10257−10253=4. That is, "−4" (−4@client) is obtained as a time synchronization correction value (to be referred to as a correction value or a time difference hereinafter) for the timer 106.

The time synchronization correction value is decided based on one inquiry in the example of FIG. 4. Since a fluctuation can occur in the propagation time in practice, a correction value based on a single inquiry may be deviated from a true amount. Therefore, as described above, it is preferable to repeat the deviation measurement between the reply time and the estimated reply time a plurality of times to statistically calculate a correction value. As an example of calculating the correction value, a method of collecting a predetermined number of time differences or correction values in the ascending order of round trip times (times from the inquiry transmission to reply reception) out of the plurality of inquiries and calculating an average of the time differences or correction values can be used.

Figure 5:
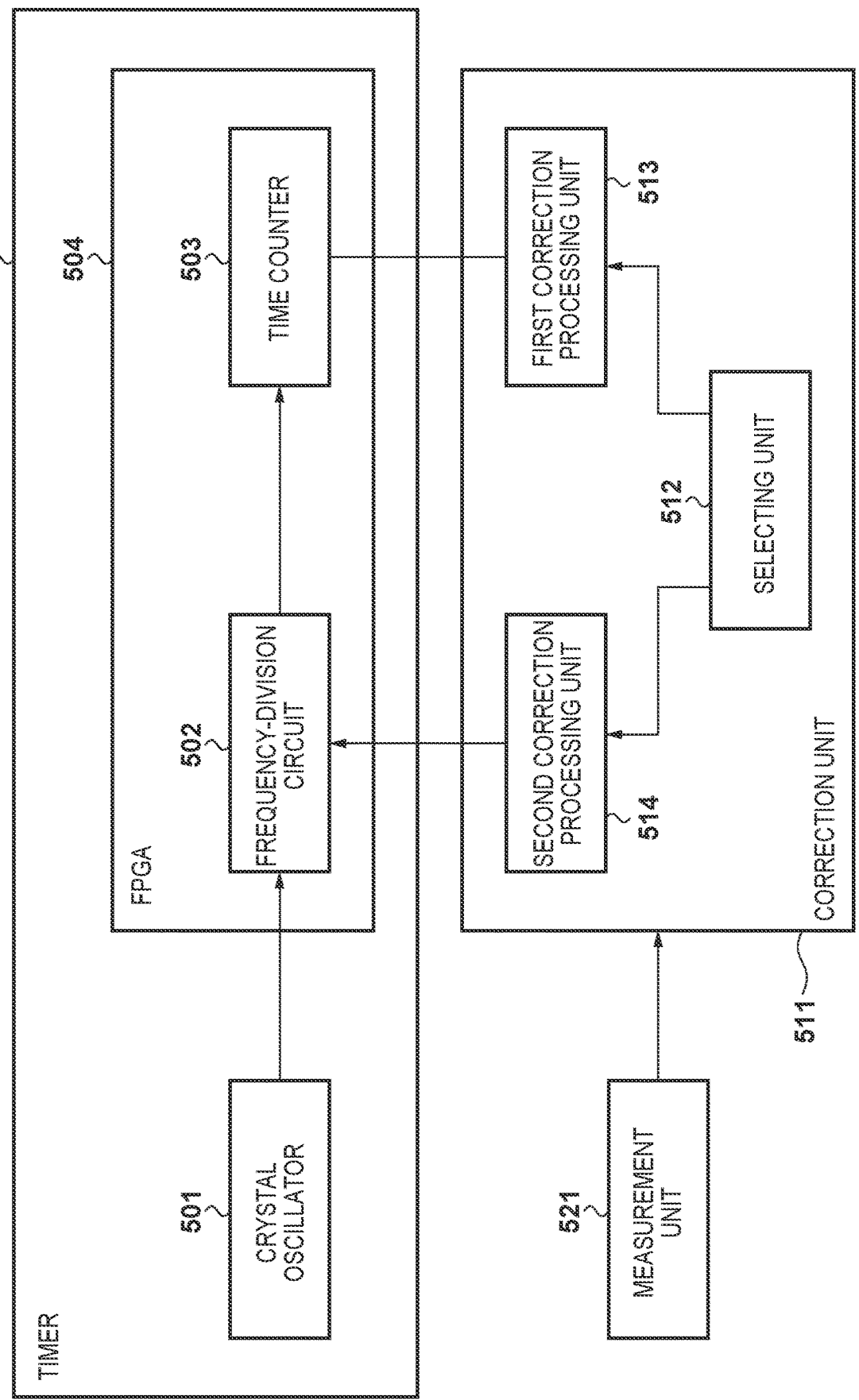
FIG. 5 is a block diagram showing the arrangement of a timer of each of the radiographic apparatus and an irradiation control apparatus.

FIG. 5 shows an example of the arrangement of each of the timer 106 and the timer 122. Each of the timer 106 and the timer 122 is formed from a crystal oscillator 501, a frequency-division circuit 502, and a time counter 503. The frequency-division circuit 502 and the time counter 503 may be implemented by an FPGA 504 serving as a programmable circuit. The FPGA stands for Field-Programmable Gate Array. By employing the FPGA 504, the division ratio of the frequency-division circuit 502 and the counter value of the time counter 503 can be changed.

According to this embodiment, by changing the division ratio of the frequency-division circuit 502 or the counter value of the time counter 503 based on the above correction value, the times of the timer 106 and the timer 122 can be synchronized. Note that the timer 106 and the timer 122 have the same arrangement, that is, an arrangement in which the division ratio or the counter value can be changed in at least one timer (that is, the timer serving as the time adjustment target). In this embodiment, at least the timer 106 has the arrangement shown in FIG. 5, and the imaging control unit 102 includes the correction unit 511 and the measurement unit 521. Note that the FPGA 504 is used to be limited to the timer 106 and the timer 122, but the FPGA 504 may include a circuit for implementing other functions of the radiographic apparatus 101 or the irradiation control apparatus 120.

In each of the timers 106 and 122, the crystal oscillator 501 includes a crystal which oscillates at a predetermined period upon reception of a voltage and generates a reference clock. The frequency-division circuit 502 divides the frequency of the reference clock and generates a clock suitable for the time counting of the radiographic system 100. The time counter 503 counts the clocks generated by the frequency-division circuit 502 to output the counter value. The counter value is a time value output by each of the timers 106 and 122. The radiographic apparatus 101 operates with reference to the counter value (time value) of the time counter 503 of the timer 106. The irradiation control apparatus 120 operates with reference to the counter value (time value) of the counter 503 of the timer 122.

As described with reference to FIG. 4, the measurement unit 521 transmits a message (the time synchronous transmission 401) via the communication network and receives the corresponding response message (time synchronous reply 402) via the communication network. The measurement unit 521 acquires a time difference based on the message transmission time, the message reception time, and the reply time included in the response message and provides the time difference to a correction unit 511. The correction unit 511 corrects the times of the timers 106 and 122. In the correction unit 511, a selecting unit 512 selects correction processing to be executed from a plurality of correction processes (a first correction processing unit 513 and a second correction processing unit 514 in FIG. 5) having different correction periods based on the operating state of the radiographic apparatus 101. The first correction processing unit 513 performs first correction processing for eliminating the time difference (the time synchronization correction value shown in FIG. 4) measured by the measurement unit 521 by changing the counter value (time value) of the time counter 503. The second correction processing unit 514 performs second correction processing for eliminating the time difference by changing, across a plurality of counts, the division ratio (the division ratio for dividing the frequency of the reference clock output from the crystal oscillator 501 to generate a clock used for counting the time value) of the frequency-division circuit 502.

Next, a method of changing the times corresponding to the correction values in order to synchronize the counter values as the time values of the timer 106 and the timer 122, will now be described. In this embodiment, by correcting the timer 106, the timer 106 is synchronized with the timer 122. As described above, the imaging control unit 102 can execute a plurality of kinds of correction processing having different correction periods. In this embodiment, the first correction processing and the second correction processing are provided as the plurality of correction processes. The first correction processing for changing the counter value of the time counter 503 of the timer 106 to match the time of the timer 106 with the time of the timer 122 has a shorter correction period than the second correction processing for changing the division ratio of the frequency-division circuit 502 of the timer 106 to make the counter value of the timer 106 come close to the counter value of the timer 122. The selecting unit 512 switches correction processing used for time correction between the first correction processing and the second correction processing in accordance with whether, for example, the radiographic apparatus 101 is during imaging operation. More specifically, according to this embodiment, the second correction processing is selected during dynamic imaging; otherwise, the first correction processing is selected.

Figure 6:
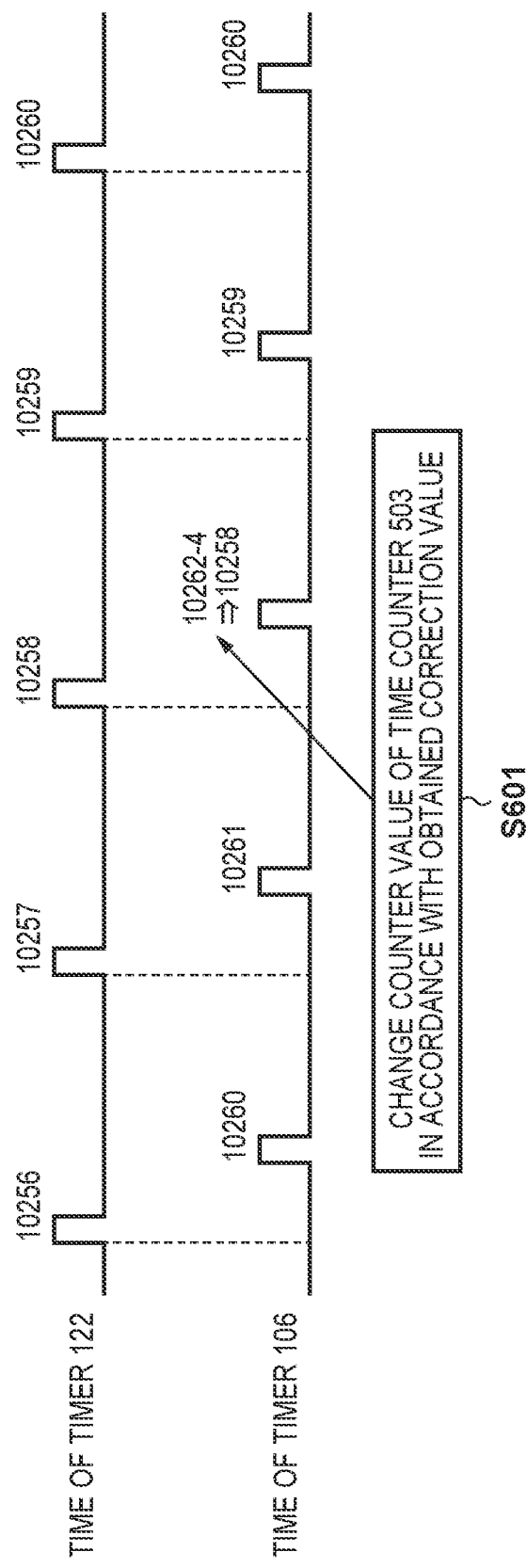
FIG. 6 is a timing chart showing a method of performing time correction by changing a time value.

FIG. 6 is a timing chart of a case (first correction processing) in which the counter value of the time counter 503 is changed to correct the timer 106. In the first correction processing, the time difference is eliminated by changing the counter value of the time counter 503 once. In FIG. 6, the irradiation control unit 124 changes the counter value of the time counter 503 of the timer 106 to 10262−4=10258 in accordance with information (FIG. 4, correction value=−4) indicating that the counter value of the timer 106 is larger than that of the timer 122 by "4" (step S601). By this change, the counter values of the time counter 503 of the timer 106 and the time counter 503 of the timer 122 are synchronized. According to this correction method, since the correction value is directly reflected on the counter value, time correction can be performed within a short time. Note that correction is complete by changing the counter value once, as described above, but the correction is not limited to this. It suffices the change in counter value can be performed within a sufficiently shorter period than the correction period of the second correction processing. The correction may be performed in a plurality of times. For example, each of two consecutive counts may be changed every half of the correction value.

Figure 7:
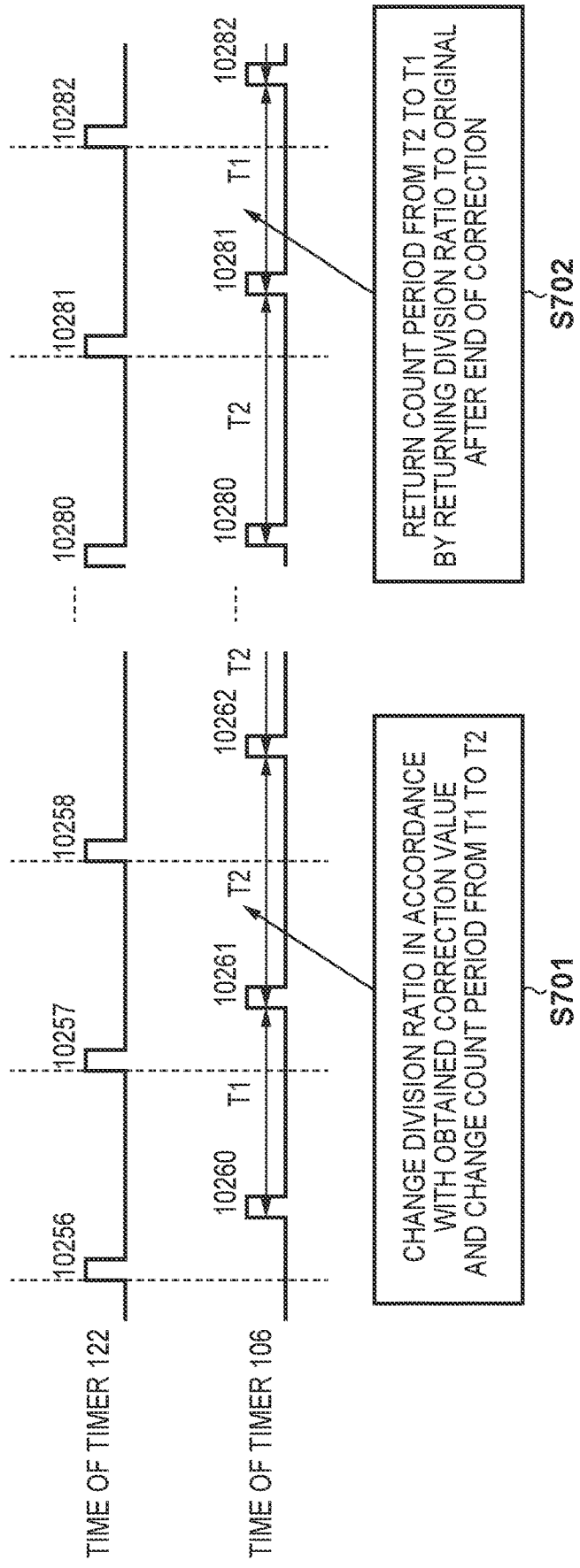
FIG. 7 is a timing chart showing a method of performing time correction by changing a division ratio of a frequency division circuit.

FIG. 7 is a timing chart when correcting a counter value by changing a division ratio of the frequency-division circuit 502 (the second correction processing). In the second correction processing, the time difference is eliminated by changing, across the plurality of clocks, the division ratio for dividing the frequency of the reference clock and generating a clock for counting the time value. The irradiation control unit 124 changes the division ratio of the frequency-division circuit 502 and changes the period of the clock input to the time counter 503. In the example of FIG. 7, the division ratio is changed from the time when the clock period T1 is changed to T2 which is 1.2 times the clock period T1 to the time when 20 clocks are counted. The 20 clocks are counted in a time of 1.2×T1×20=24 (count) (steps S701 and S702). In this manner, the state in which the counter value of the timer 106 is larger than that of the timer 122 by "4" (the state shown in FIG. 4) is corrected. In the correction method shown in FIG. 7, the time is gradually corrected in accordance with the set division ratio. For this reason, an abrupt change in time by time correction can be suppressed. Note that the arrangement shown in FIG. 5 is merely an example. The arrangement of implementing the function of the change in the count speeds of the times of the timers 106 and 122 and the function of the change in time values is not limited to the illustrated example.

Figure 8:
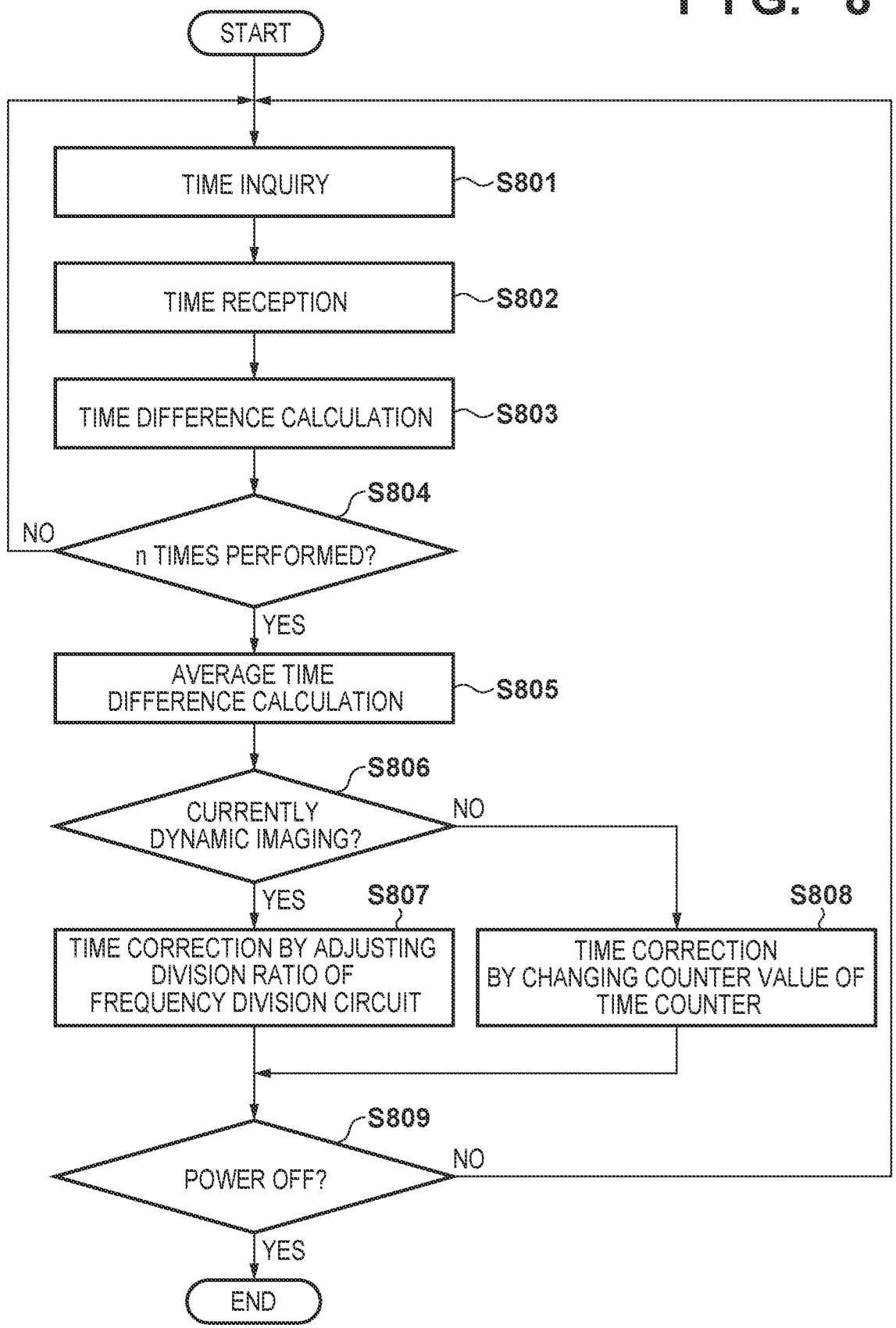
FIG. 8 is a flowchart showing time correction processing according to the first embodiment.

Next, time correction processing performed by the radiographic apparatus 101 according to the first embodiment will be described with reference to the flowchart of FIG. 8.

Steps S801 to S803 form processing for measuring a time difference between the timer 106 and the timer 122. First, in step S801, the measurement unit 521 of the radiographic apparatus 101 makes a time inquiry (the time synchronous transmission 401) to the irradiation control apparatus 120. At this time, the radiographic apparatus 101 saves the time of the timer 106 which serves as the transmission time. Next, in step S802, the measurement unit 521 receives a reply (time synchronous reply 402) corresponding to the time inquiry from the irradiation control apparatus 120. At this time, the measurement unit 521 saves the time of the timer 106 which serves as the reception time. The time synchronous reply 402 includes the time (reply time) of the timer 122 obtained when the irradiation control apparatus 120 transmits the time synchronous reply 402. In step S803, the measurement unit 521 calculates the estimated reply time from the transmission time and the reception time and compares this with the reply time to calculate the time difference. Note that the estimated reply time is obtained by calculating (reception time−transmission time)/2 as described above with reference to FIG. 4.

The measurement unit 521 repeats the operation above time difference calculation (steps S801 to S803) a plurality of times (n times in this embodiment) so as to obtain a time difference with sufficient precision (step S804). In step S805, the measurement unit 521 calculates an average time difference from the obtained n time differences.

Next, in step S806, the selecting unit 512 of the correction unit 511 of the radiographic apparatus 101 determines based on the imaging request 201 sent from the irradiation control apparatus 120 and the stop request 302 whether dynamic imaging is being performed. If it is determined that dynamic imaging is being performed, the process advances to step S807. In step S807, the selecting unit 512 selects the second correction processing unit 514, and the correction unit 511 changes the division ratio of the frequency-division circuit 502 of the timer 106 to correct the time difference between the timer 106 and the timer 122. On the other hand, if it is determined in step S806 that dynamic imaging is not being performed, the process advances to step S808. In step S808, the selecting unit 512 selects the first correction processing unit 513, so that the correction unit 511 directly changes the counter value of the time counter 503 of the timer 106 to perform time correction. After the time correction, if the power supply is not turned off, the process returns to step S801 to correct the shifted time again (step S809). Note that the sequence of the processing in dynamic imaging has been described in the example of FIG. 8, but the same method can be used even in static imaging.

Figure 9:
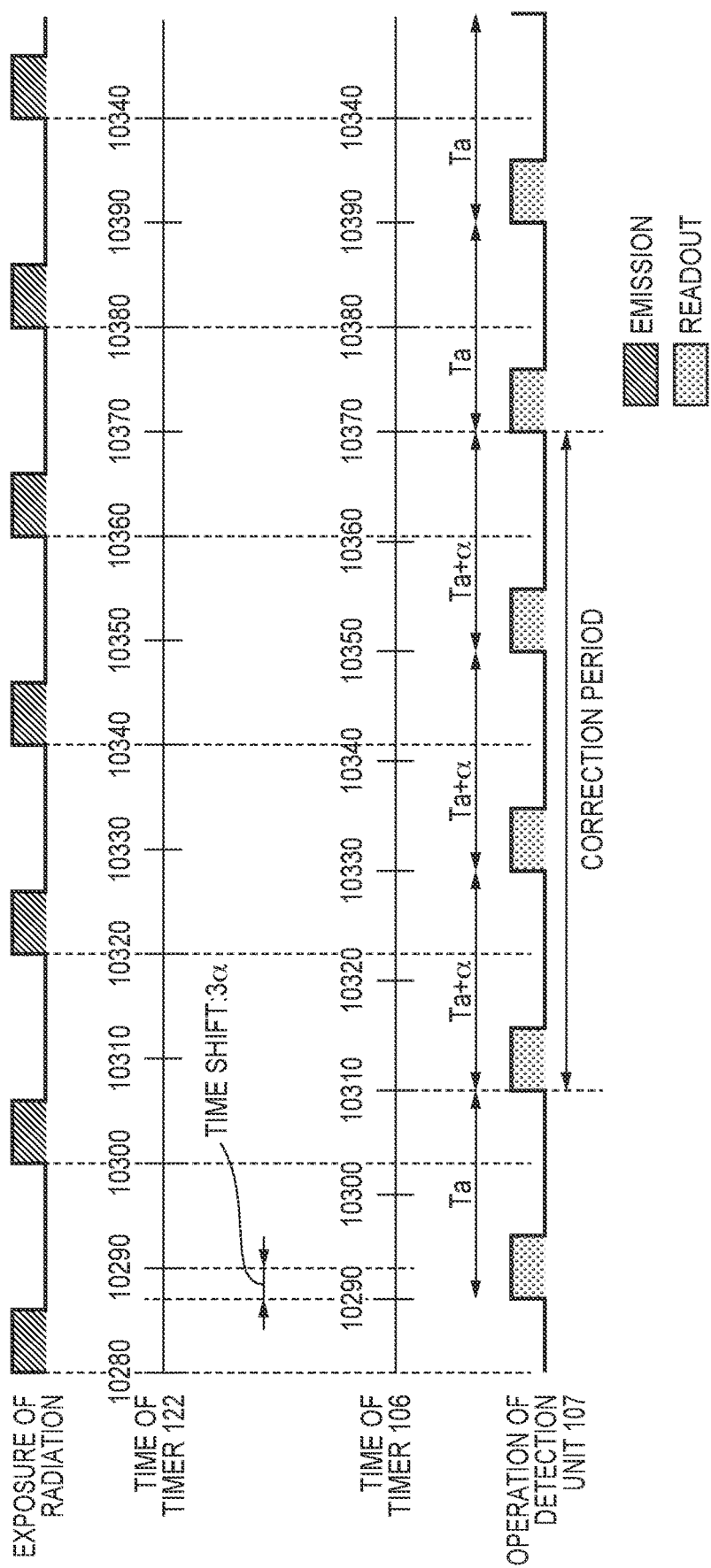
FIG. 9 is a timing chart showing a time correction operation in dynamic imaging according to the first embodiment.

FIG. 9 is a timing chart showing the second correction processing (step S807) for correcting the average time difference between the timers 106 and 122 by changing the division ratio of the frequency-division circuit 502. This operation is the second correction processing described above. In the example of FIG. 9, in order to correct an average time difference 3α, a state is shown in which the division ratio of the frequency-division circuit 502 of the timer 106 is adjusted so that the time count of the timer 106 is smaller than that of the timer 122. A correction period until the average time difference 3α is corrected is estimated from the adjustment value of the division ratio, and the adjustment of the division ratio is maintained during the estimated correction period. When the correction period has elapsed, the division ratio is returned to the value before the adjustment, thereby ending the time correction. In the example of FIG. 9, the normal time required to cause the time counter 503 count 20 clocks is Ta, and the time required to count 20 clocks by adjusting the division ratio of the frequency-division circuit 502 is Ta+α. That is, the time required for one count is prolonged by α/20 by the adjustment of the division ratio. If the average time difference is 3α, the correction period is a period of 60 counts. The correction period started from a counter value "10310" ends in the counter value "10370".

As a result, in the example of FIG. 9, the original accumulation time is a "Ta−readout time", and the accumulation time between the correction periods is a "Ta+α−readout time", then the change in accumulation time in dynamic imaging is +α. Since the change in accumulation time obtained when the time difference 3α is corrected at once is +3α, it is possible to further reduce the change in accumulation time. The change in accumulation time is a change in time for which charges in the detection unit 107 are accumulated. The change in accumulation time influences the pixel value of the radiation image output from the radiographic apparatus 101. For this reason, since the change in accumulation time is suppressed to be a small value, time correction is executed while the influence on the pixel value is suppressed. The adjustment value of the division ratio and the correction period are desirably values by which the influence on the pixel value of the radiation image does not influence the use such as diagnosis. If parameters such as a gain and a frame rate have a plurality of predetermined types of imaging modes, it is possible to change the adjustment value of the division ratio and the correction period in accordance with an imaging mode. Note that the start of time correction is matched with the operation (start of readout) of the detection unit 107 in the example of FIG. 9, but such matching need not be performed.

Figure 10:
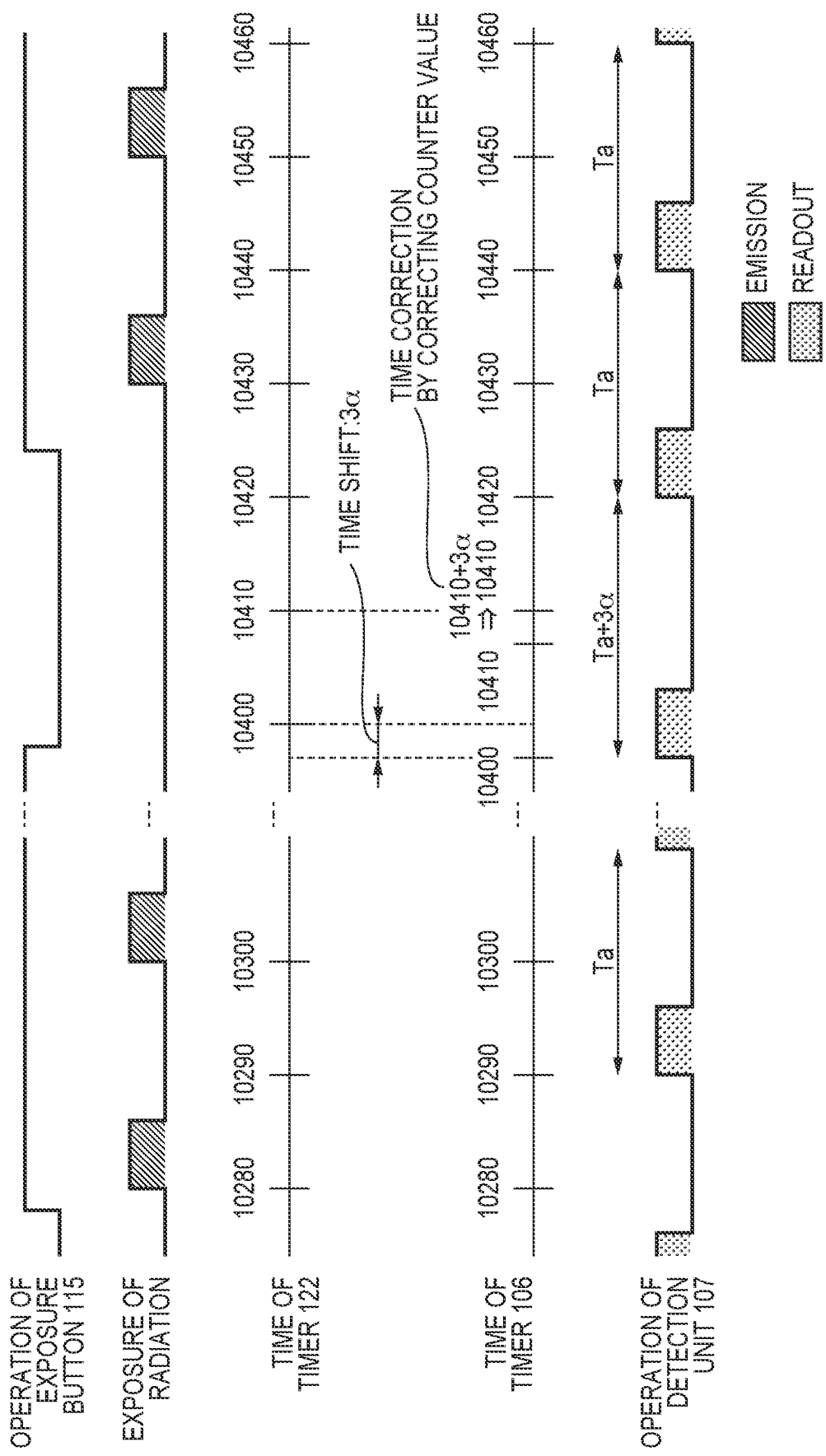
FIG. 10 is a timing chart showing a time correction operation in a period other than dynamic imaging.

FIG. 10 is a timing chart showing the operation of the first correction processing (step S808) for performing time correction in a method of directly changing the counter value of the time counter 503 of the timer 106. This operation is the first correction processing described above. As shown in FIG. 10, the time correction by changing the counter value is performed while the exposure button 115 is released (a period between dynamic imaging and dynamic imaging). The time of the timer 106 is corrected at 10410+3α. At this time, the time counter 503 of the timer 106 is changed to 10410 to immediately complete the time correction. By this time correction, the accumulation time becomes Ta+3α. Since this time includes a timing at which imaging is not performed, no influence is imposed on the radiation image output from the radiographic apparatus 101.

Note that in the first embodiment, a method of correcting the time across a plurality of time counts by adjusting the division ratio of the frequency-division circuit 502 has been described as the second correction processing. However, the second correction processing is not limited to this. For example, the calculated time difference between the timer 106 and the timer 122 may be corrected (eliminated) by changing the counter value a plurality of times (every predetermined count). For example, in the example of FIG. 9, the counter value may be changed a plurality of times to correct the time difference 3α. For example, as shown in FIG. 9, every time the time counter 503 performs counting of 20 clocks, the counter value of the time counter 503 may be changed by a value corresponding to the time a, thereby correcting the counter value of the timer 106. In addition, in FIG. 9, the correction period is decided by the adjustment amount of the preset division ratio to perform time correction. However, the time correction is not limited to this method. For example, the correction period may be preset, and the adjustment amount of the division ratio may be decided in accordance with the average correction value and the correction period. In addition, the adjustment amount of the division ratio may be decided in accordance with the frame rate of dynamic imaging. In this case, for example, the dividing ratio may be adjusted such that a change in time per frame is a predetermined ratio (for example, 5%). These modifications can be applied when time correction is performed by changing the counter value every predetermined count. In addition, for example, when an operating state is changed during the correction period of the second correction processing, the remaining time difference may be corrected by the first correction processing. In addition, in the first embodiment, the time of the timer 106 is corrected using the timer 122 as a reference, but the time of the timer 122 may be corrected using the timer 106 as a reference.

As described above, according to the first embodiment, the imaging control unit 102 measures the time difference between the timer 106 and the timer 122 and corrects the timer 106 so as to eliminate the measured time difference. The imaging control unit 102 can execute a plurality of types of corrections having different correction periods, as described with reference to, for example, FIGS. 6 and 7. The imaging control unit 102 corrects the timer 106 using correction process selected from the plurality of correction processes based on the operating state (for example, whether or not dynamic imaging is being performed) of the radiographic apparatus 101. Accordingly, appropriate time synchronization corresponding to the operating state of the radiographic apparatus can be performed.

Second Embodiment

The first embodiment has explained the arrangement in which the time correction methods are switched in accordance with whether dynamic imaging is being performed. The second embodiment will describe an arrangement for switching time correction methods in accordance with an offset correction mode (to be referred to as a dark correction mode hereinafter) in dynamic imaging. That is, in the second embodiment, the dark correction mode is used as a correction processing selection condition in addition to whether a radiographic apparatus 101 is performing dynamic imaging. Note that the arrangement of the radiographic system, the arrangement about time correction, and the principle of the correction operation of the radiographic system according to the second embodiment are the same as those of the first embodiment (FIGS. 1 to 7). Parts different from the first embodiment will mainly be described below.

Figure 11:
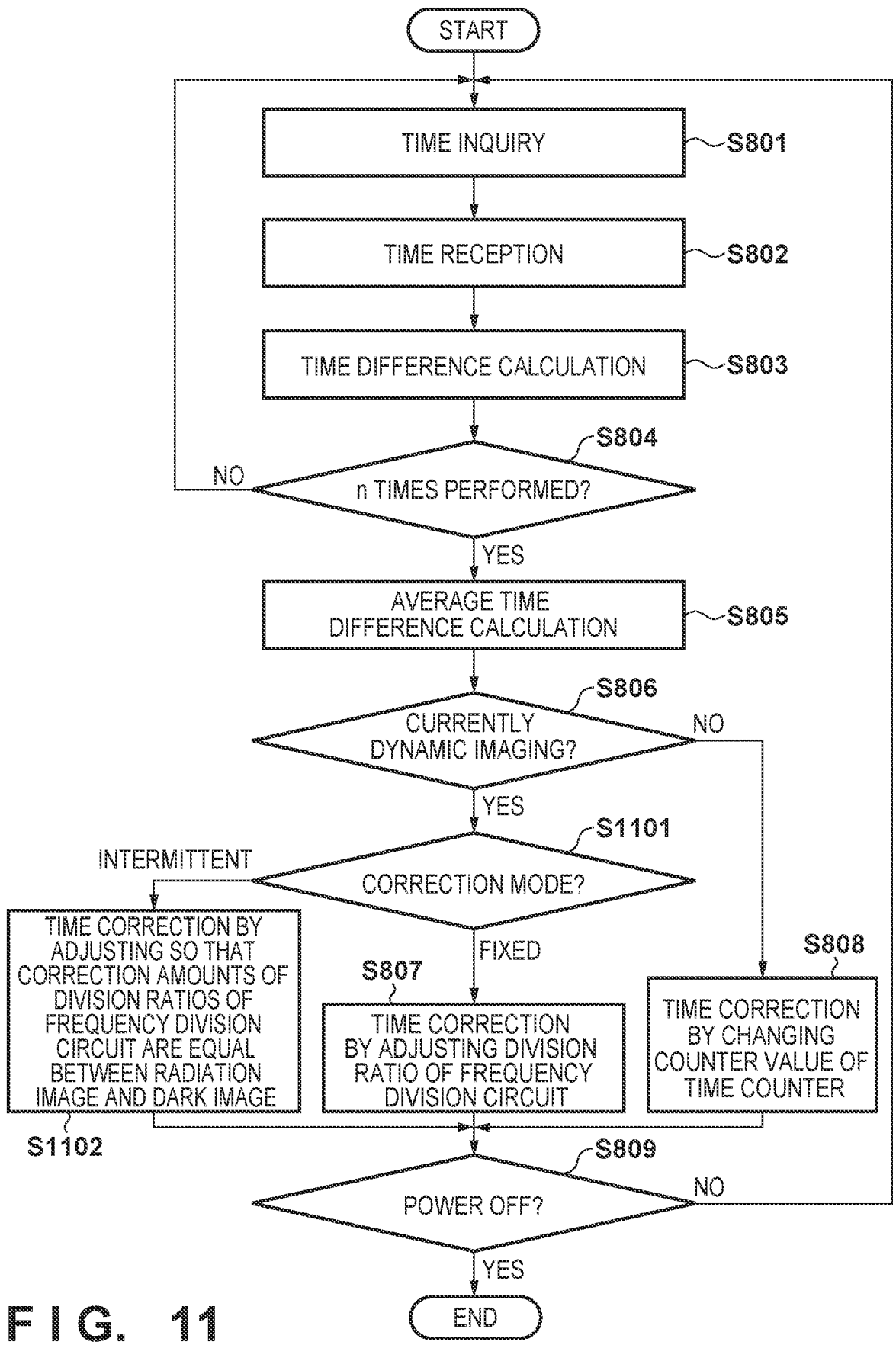
FIG. 11 is a flowchart showing time correction processing according to the second embodiment.

FIG. 11 is a flowchart showing time synchronization processing performed by the radiographic apparatus 101 according to the second embodiment. Processing in steps S805 to S806 and S808 is the same as in the first embodiment (FIG. 8). If it is determined in step S806 that dynamic imaging is being performed, the radiographic apparatus 101 determines in step S1101 that a selecting unit 512 selects the offset correction mode. The selecting unit 512 according to the second embodiment switches a time correction method in accordance with the determination result of the offset correction mode.

The offset correction is a correction method of calculating a difference between a radiation irradiation image (to be referred to as a radiation image hereinafter) and a radiation non-irradiation image (to be referred to as a dark image hereinafter) in order to correct charges generated without radiation irradiation by a detection unit 107. The radiographic apparatus 101 according to the second embodiment has a fixed dark correction mode and an intermittent dark correction mode as the dark correction modes. The fixed dark correction mode is a correction mode in which a dark image is acquired and saved in advance, and the dark image saved at the time of offset correction is read out and used. The intermittent dark correction is a correction mode in which dark images are acquired before and after the imaging of the radiation image, and the dark image is used at the time of correction. The operator or a radiographic system 100 can arbitrarily switch a correction mode in accordance with a situation.

If it is determined in step S1101 that the correction mode is the fixed dark correction mode, the selecting unit 512 performs time correction (second correction processing) in step S807 as in the first embodiment. For example, the time difference between a timer 106 and a timer 122 is corrected by adjusting the division ratio of a frequency-division circuit 502 of the timer 106. On the other hand, if it is determined in step S1101 that the correction mode is the intermittent dark correction, the process advances to step S1102. In step S1102, the selecting unit 512 selects a third correction processing unit (not shown) and causes the unit to perform third correction processing. In the third correction processing, the division ratio of the frequency-division circuit 502 of the timer 106 is adjusted so that the correction amounts of the division ratios are equal between the radiation image and the dark image, thereby correcting the time. As a result, according to the correction processing selected in step S1102, in order to eliminate the time difference, the timer 106 is changed such that the imaging time of the radiation image is set equal to the imaging time of the dark image used for offset correction of the radiation image. Note that as described with reference to the first embodiment, the counter value of the time counter 503 may be changed a plurality of times in place of changing the division ratio.

Figure 12:
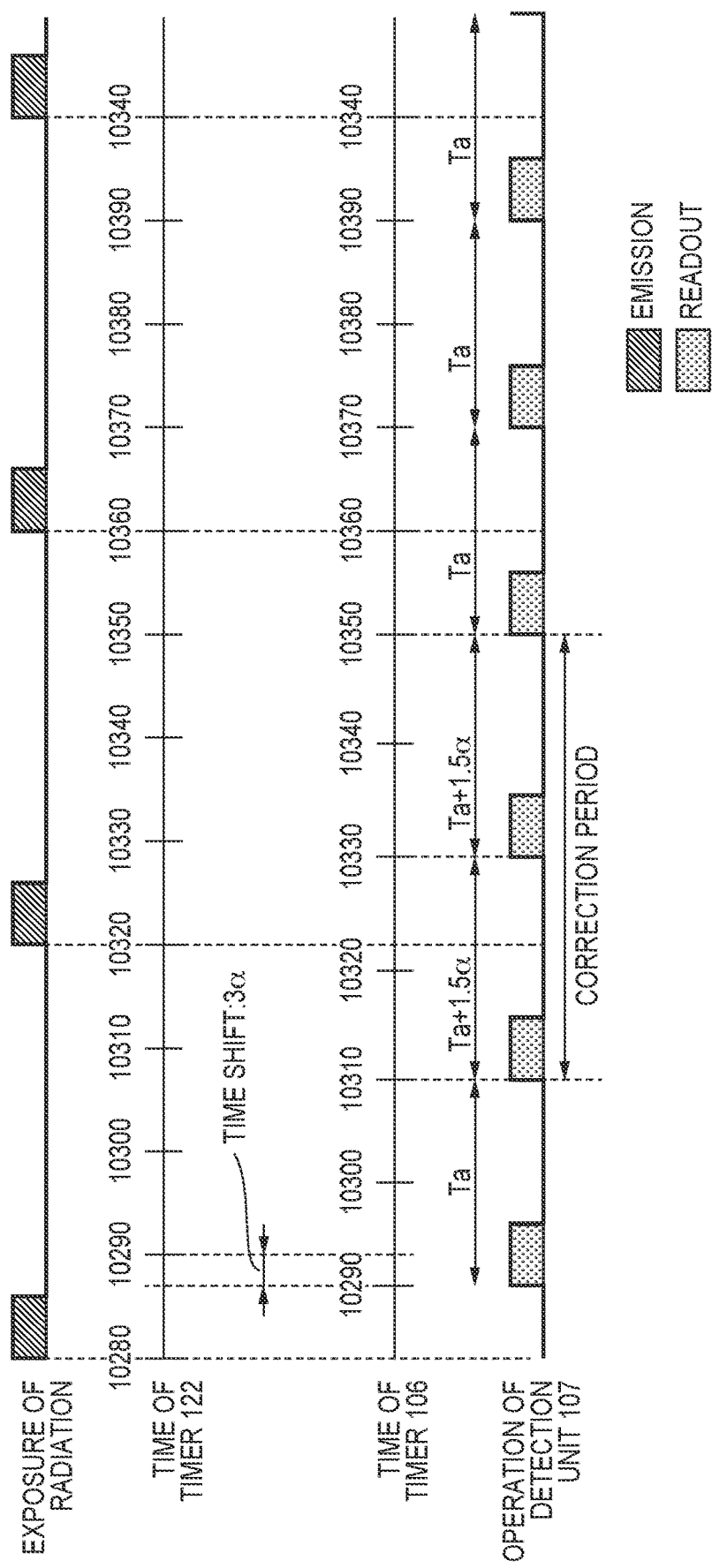
FIG. 12 is a timing chart showing a time correction operation during dynamic imaging in an intermittent dark correction mode.

FIG. 12 is a timing chart showing a time correction operation by a correction unit 511 in the intermittent dark correction mode (in this embodiment, the correction dark image is acquired after the radiation irradiation image). In the example of FIG. 12, dynamic imaging is performed while the radiation image and the dark image are alternately acquired. The correction period is determined to perform time correction such that the correction amounts for the time deviation 3α are set equal between the acquisition of the radiation irradiation image and the acquisition of the radiation non-irradiation image. As a result, each of the accumulation times of the radiation irradiation image and the radiation non-irradiation image per frame becomes Ta+1.5α. Accordingly, the extra charges stored in the period of +1.5α can be removed by the offset correction. For this reason, the time correction can be performed within a short time while preventing an increase/decrease in the pixel value due to an accumulation time difference in frames before and after the correction of dynamic imaging.

Note that in the second embodiment, a case in which the dark image to be used is obtained immediately after imaging of the radiation image. The same arrangement and processing can be obviously applied even in a case in which a dark image obtained immediately before the imaging of the radiation image is used. In addition, according to the second embodiment, a case in which the radiation image and the dark image are alternately obtained has been described, but the dark image acquisition timing is not limited to this. For example, if one dark image is applied to several radiation images or an average value of several dark images is used, the same method as described above can be used. For example, when n dark images are obtained for one radiation image, or one dark image is acquired for n radiation images, the time correction is performed such that the average time difference is distributed in the acquisition periods of the (n+1) images. In addition, according to the second embodiment, a method of correcting the time across a plurality of time counts by adjusting the division ratio of the frequency-division circuit 502 has been described. However, a method of correcting the counter value by dividing the calculated time difference between the timer 106 and the timer 122 a plurality of steps may be used.

As described above, according to each embodiment described above, the time difference in time synchronization can be limited by an appropriate method in accordance with the operating state of the radiographic apparatus. That is, according to each embodiment, the timer for obtaining the timing of radiation irradiation and the timer for obtaining the timing of the radiation imaging can be more appropriately synchronized.

OTHER EMBODIMENT

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-024336, filed Feb. 14, 2018, which is hereby incorporated by reference herein in its entirety.

What is claimed is:

1. A radiographic system in which an irradiation control apparatus configured to control irradiation of radiation and a radiographic apparatus configured to perform radiation imaging are communicably connected, the system comprising:

a first timer incorporated in the irradiation control apparatus and configured to provide a time value for an irradiation timing;

a second timer incorporated in the radiographic apparatus and configured to provide a time value for an imaging timing;

a measurement unit configured to measure a time difference between a time value of the first timer and a time value of the second timer;

a correction unit configured to correct at least one timer out of the first timer and the second timer so as to eliminate the time difference, the correction unit capable of executing a plurality of types of correction processing having different correction periods; and a selecting unit configured to select, from the plurality of types of correction processing, correction processing to be executed by the correction unit, based on an operating state of the radiographic apparatus.

2. The system according to according to claim 1, wherein the plurality of types of correction processing include first correction processing configured to eliminate the time difference and second correction processing configured to eliminate the time difference in a longer correction period than that of the first correction processing, and the selecting unit selects the second correction processing if the radiographic apparatus is being in an imaging operation, and otherwise selects the first correction processing.

3. The system according to claim 2, wherein the first correction processing eliminates the time difference by changing a time value of one of the first timer and the second timer once.

4. The system according to claim 2, wherein the second correction processing eliminates the time difference by changing, across a plurality of clocks, a division ratio used when dividing a frequency of a reference clock in the one timer to generate a clock for counting a time value.

5. The system according to claim 2, wherein the second correction processing eliminates the time difference by changing a time value of the one timer a plurality of times.

6. The system according to claim 2, wherein a correction period of the second correction processing is set based on a frame rate of imaging.

7. The system according to claim 1, wherein the selecting unit selects, from the plurality of pieces of correction processing, correction processing to be executed by the correction unit, based on an employed dark correction mode if the radiographic apparatus is being in imaging.

8. The system according to claim 1,
further comprising third correction processing configured to correct the one timer so that an imaging time of a dark image is set equal to that of a radiation image,
wherein the selecting unit selects, from the plurality of pieces of correction processing, correction processing to be executed by the correction unit, based on an employed dark correction mode if the radiographic apparatus is being in imaging.

9. The system according to claim 1, wherein the measurement unit obtains the time difference by averaging a plurality of measurement results.

10. The system according to claim 1,
further comprising a communication unit configured to perform communication between the irradiation control apparatus and the radiographic apparatus,
wherein the measurement unit acquires a time difference based on time at which the communication unit transmits a message from one of the irradiation control apparatus and the radiographic apparatus, time at which a corresponding response message is received via the communication unit, and reply time included in the response message.

11. A radiographic apparatus that performs radiation imaging using radiation emitted from an irradiation control apparatus, comprising:
a communication unit configured to communicate with the irradiation control apparatus;
a timer unit configured to provide a time value for a timing of the radiation imaging;
a measurement unit configured to measure a time difference between the time value of the timer unit and a time value of a timer of the irradiation control apparatus by communication via the communication unit;
a correction unit configured to correct the timer unit so as to eliminate the time difference, the correction unit capable of executing a plurality of pieces of correction processing having different correction periods; and
a selecting unit configured to select, from the plurality of pieces of correction processing, correction processing to be executed by the correction unit, based on an operating state of the radiographic apparatus.

12. A control method for a radiographic system in which an irradiation control apparatus incorporating a first timer that provides a time value for an irradiation timing and configured to control irradiation of radiation and a radiographic apparatus incorporating a second timer that provides a time value for imaging timing are communicably connected to each other, the method comprising:
measuring a time difference between the time value of the first timer and the time value of the second timer;
selecting, from a plurality of types of correction processing having different correction periods, correction processing based on an operating state of the radiographic apparatus, the selected correction processing being configured to correct at least one of the first timer and the second timer so as to eliminate the time difference; and
executing the selected correction processing.

13. A control method for a radiographic apparatus including a communication unit configured to communicate with an irradiation control apparatus and timer unit configured to provide a time value for a timing of radiation imaging, the radiographic apparatus performing the radiation imaging using radiation emitted from the irradiation control apparatus, the method comprising:
measuring a time difference between the time value of the timer unit and a time value of a timer of the irradiation control apparatus by communication via the communication unit;
selecting, from a plurality of types of correction processing having different correction periods, correction processing based on an operating state of the radiographic apparatus, the selected correction processing being configured to correct the timer unit so as to eliminate the time difference; and
executing the selected correction processing.

14. A non-transitory computer-readable storage medium storing a program for causing a computer to execute a control method for a radiographic apparatus including a communication unit configured to communicate with an irradiation control apparatus and timer unit configured to provide a time value for a timing of radiation imaging, the radiographic apparatus performing the radiation imaging using radiation emitted from the irradiation control apparatus, the method comprising:

measuring a time difference between the time value of the timer unit and a time value of a timer of the irradiation control apparatus by communication via the communication unit;

selecting, from a plurality of types of correction processing having different correction periods, correction processing based on an operating state of the radiographic apparatus, the selected correction processing being configured to correct the timer unit so as to eliminate the time difference; and executing the selected correction processing.

* * * * *